United States Patent [19]
Vachon et al.

[11] Patent Number: 5,324,324
[45] Date of Patent: Jun. 28, 1994

[54] COATED IMPLANTABLE STIMULATION ELECTRODE AND LEAD

[75] Inventors: David J. Vachon, Granada Hills; John R. Helland, Saugus, both of Calif.

[73] Assignee: Siemens Pacesetter, Inc., Sylmar, Calif.

[21] Appl. No.: 960,670

[22] Filed: Oct. 13, 1992

[51] Int. Cl.⁵ .................................. A61N 1/05
[52] U.S. Cl. .................................... 607/120
[58] Field of Search ............... 607/119, 120, 121, 122; 128/642

[56] References Cited

U.S. PATENT DOCUMENTS

| | | | |
|---|---|---|---|
| 4,033,357 | 7/1977 | Helland et al. | 607/121 |
| 4,281,668 | 8/1981 | Richter et al. | 607/121 |
| 4,506,680 | 3/1985 | Stokes | 607/120 |
| 4,606,118 | 8/1986 | Cannon et al. | 29/825 |
| 4,711,251 | 12/1987 | Stokes . | |
| 4,827,940 | 5/1989 | Mayer et al. | 128/642 |
| 4,844,099 | 7/1989 | Skalsky et al. . | |
| 4,953,564 | 9/1990 | Berthelsen . | |
| 5,103,837 | 4/1992 | Weidlich et al. | 607/120 |

Primary Examiner—Lee S. Cohen
Assistant Examiner—Jeffrey R. Jastrzab
Attorney, Agent, or Firm—Malcolm J. Romano

[57] ABSTRACT

An implantable stimulation lead having an anti-inflammatory coating on the exposed surface area of the distal tip electrode. The coating is a semi-viscous or gelatinous material having the ability to absorb physiological fluids to provide electrical conductivity through the coating. The coating preferably has a matrix having an innate hypo-inflammatory property which can be combined with drugs and therapeutic agents to deliver the drugs and agents by co-dissolution or diffusion, or alternatively the matrix material can be used as a coating to keep the electrode surface electrochemically clean prior to and during implant.

5 Claims, 1 Drawing Sheet

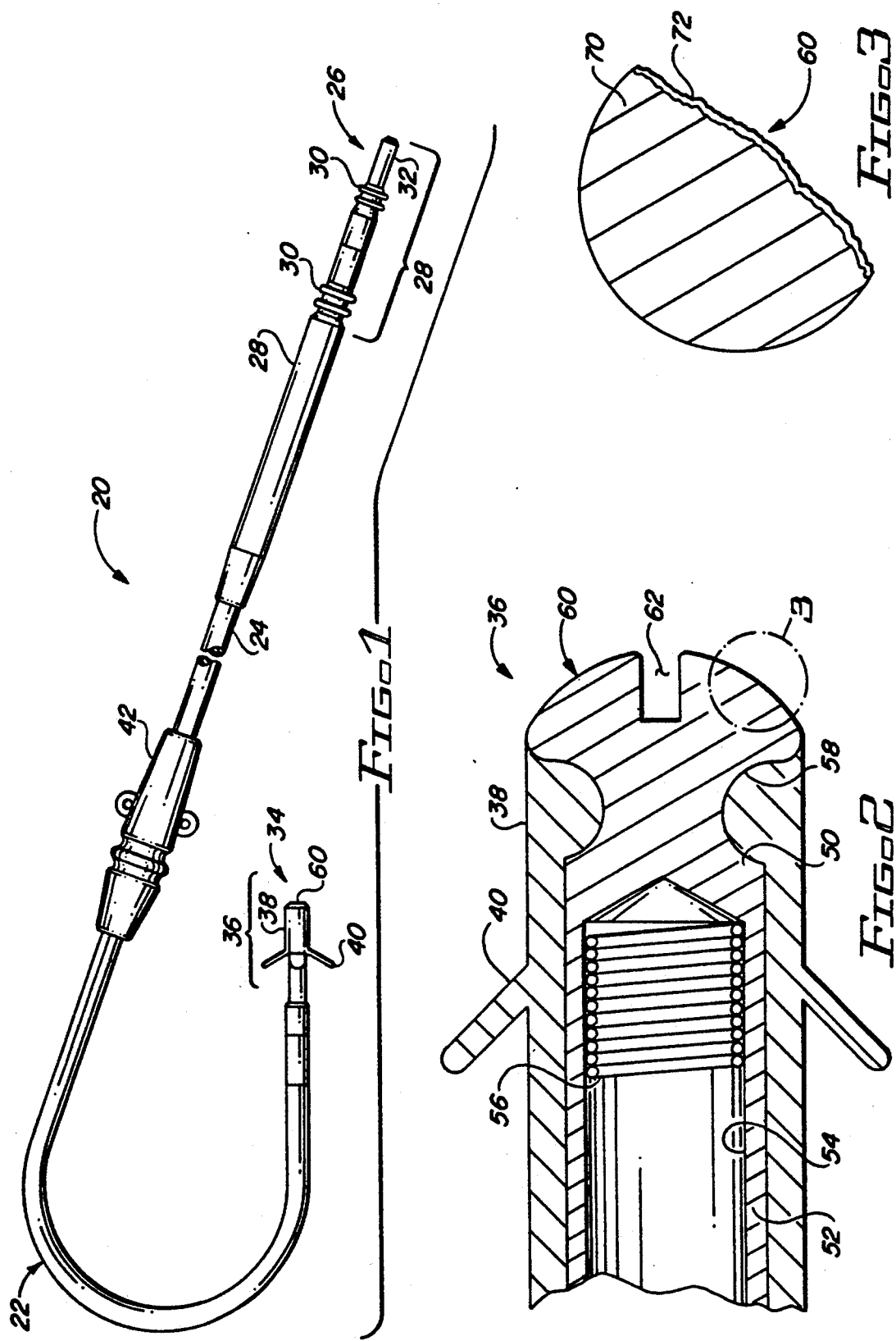

COATED IMPLANTABLE STIMULATION ELECTRODE AND LEAD

CROSS-REFERENCE TO RELATED APPLICATIONS

This application is related to copending patent application, entitled "COMPOUND AND METHOD OF APPLYING ANTI-FOULING COATINGS ON MEDICAL DEVICES," Ser. No. 07/960,669 filed Oct. 13, 1992.

FIELD OF THE INVENTION

This invention relates generally to an implantable stimulation lead for use with an implantable pulse generator such as a cardiac pacemaker. More specifically, the invention relates to an implantable stimulation lead having a viscous coating on the distal tip electrode to prevent, inhibit, or suppress inflammation; and a method of making the coated electrode.

BACKGROUND OF THE INVENTION

For a cardiac pacemaker, functional implant life time is, in part, determined by the energy delivered per pulse. The pacemaker will have a longer life if the energy delivered per pulse can be maintained at a minimum. The design of an implantable pacing lead which is used with the pacemaker is influenced by the electrical signal required for pacing stimulation. Preferably, a key design objective for a pacing lead should be the maximization of stimulation energy with minimum battery current drain over the life of the pacemaker. These objectives therefor require considerations of the lead's electrode design, geometry, and pacing threshold minimization.

Generally, pacing leads have utilized electrically conductive metals such as a platinum, platinum-iridium, or carbon composition for the tip electrode. Physiologically, a cardiac pacemaker must be capable of generating a signal with a sufficient magnitude to depolarize the excitable cells of the myocardium to initiate contraction. The electrode shape, size, surface nature, and material; the body fluid or electrolyte conductivity; and the distance separating the electrode and the excitable cardiac tissue, combine to determine the energy required of the pacemaker. Thus, the main factors to be considered with regard to the design of an implantable pacing lead are: shape, size, surface nature, materials, fixation of the electrode, and the cardiac tissue reaction.

The pacing or stimulation threshold is a reflection of the energy required for a pulse to initiate and maintain consistent cardiac contractions. When a lead is implanted, the stimulation threshold generally is at a relatively low level and then rises for a period of a few weeks after the implant of the lead. The typical rise in the threshold has been believed to be a result of an increase in the spacing between the electrode and the excitable cardiac tissue. It is generally believed that the spacing increase occurs primarily due to the inflammatory response and the subsequent development of a fibrous capsule around the electrode tip.

One factor which influences the development of the fibrous capsule is the constant beating of the heart, which causes the electrode to pound against the endocardium, causing irritation. Additionally, any rough surface structure of the electrode tip may be abrasive on the abutting tissue, causing still further irritation. The irritation of the endocardial tissue, as well as the patient's natural foreign body reaction to the presence of the electrode, results in the initiation of the inflammatory response and the subsequent fibrous capsule to develop and increase in thickness as an attempt by the body to wall-off the foreign material. Thus, thickness of the fibrous capsule is also dependent upon the geometry, materials, and structure of the electrode tip, and the foreign body reaction process.

In order to counter, delay or suppress the occurrence of the inflammatory response and therefore the growth of the fibrous capsule, pacing leads have been developed which include a drug or steroid-eluting tip electrode structure. Examples of these types of leads include U.S. Pat. Nos. 4,606,118 (Cannon et al.); 4,711,251 (Stokes); 4,844,099 (Skalsky et al.) and 4,953,564 (Berthelsen). These patents generally detail implantable leads which include a reservoir which is located typically within the tip electrode structure proximate to the distal tip electrode. The drugs are dispensed usually through a porous media of the tip electrode. Typically, the drug is intended to counter thrombus formation, fibrosis, inflammation, or arrhythmias, or any combination thereof.

As alternative designs, the U.S. Pat. No. 4,711,251 depicts a sintered electrode material having a high surface area on which the drug to be dispensed is deposited in a solid form as a coating. A solid composite material including the drug may also be employed to form the sheath and/or the tines of the electrode is also disclosed. In either of these alternative designs, the coating or composite is fixed in a solid form, i.e., they have a fixed geometry. In this configuration, the solid materials will not act as lubricants between the metallic electrode and the endocardial tissue.

While these designs for pacing leads attempt to reduce and delay the inflammatory response and the growth of the fibrous capsule, their effectiveness leaves much to be desired. In view of the above characteristics of an electrode for a cardiac pacemaker, minimal tissue reaction is desired around the tip, but high electrical coupling of the electrode to the tissue is essential. An electrode for a pacing lead which satisfies both of these criteria, and which also has the ability to deliver specific drugs to the endocardial tissue, is therefor highly desirable.

SUMMARY OF THE INVENTION

The present invention is directed to an implantable pacing lead for use with a cardiac pacemaker which has a biocompatible coating applied to the exposed surface area of the distal tip electrode to suppress or reduce the inflammatory response and growth of the fibrous capsule. By comparison to an uncoated electrode or an electrode coated only with a steroid, the biocompatible coating tends to mediate the acute inflammatory response to the presence of the electrode. The coating is formed as a viscous or gelatinous composite material having a hydrophilic property providing the ability to absorb physiological fluids. Absorption of physiological fluids provides electrical conductivity through the coating, allowing current to be delivered from the distal tip electrode to the excitable tissue with minimal impairment. By the time the viscous coating is resorbed, the healing process following the acute phase of inflammation has started and the resulting fibrotic capsule is diminished.

The coating preferably has an innate hypo-inflammatory property, and is used to keep the electrode tip clean prior to and during implant so as not to effect the electrical properties of the electrode. Preferred coating materials include such substances as albumin, collagen, and gelatin. Alternative materials are also contemplated. These materials can be combined with drugs and therapeutic agents to deliver the drugs and agents by co-dissolution or diffusion.

BRIEF DESCRIPTION OF THE DRAWINGS

FIG. 1 shows a side plan view of a pacing lead according to the present invention.

FIG. 2 shows a cross-sectional view of the distal tip of the electrode of the lead shown in FIG. 1.

FIG. 3 shows an enlarged partial cross-sectional view of a portion of the distal tip of the electrode of the lead shown in FIG. 2.

DETAILED DESCRIPTION OF THE PREFERRED EMBODIMENT

While the present invention will be described in conjunction with an endocardial pacemaker lead, it is understood that the coatings described herein could be used on other implantable electrodes, such as defibrillator electrodes, for reducing inflammation.

FIG. 1 shows a side plan view of a pacing lead 20 according to the present invention. The lead 20 is provided with an elongated lead body 22 which includes electrical conductors (not shown) covered with an insulation sheath 24. The insulation sheath is preferably fabricated of silicone rubber, polyurethane or other suitable polymer. At a proximal end 26 of the pacing lead 20 is a connector assembly 28, which is provided with sealing rings 30 and which carries at least one electrical connector 32. The connector assembly 28 is constructed using known techniques and is preferably fabricated of silicone rubber, polyurethane or other suitable polymer for insulation. Connector 32 is preferably fabricated of stainless steel or other suitable conductive material.

At a distal end 34 of the pacing lead 20 is an electrode assembly 36 which is discussed in more detail below. Immediately behind the distal end of the electrode assembly 36 is a tine sheath 38 which includes a plurality of individual tines 40. Tines 40 engage endocardial tissue and urge a distal tip electrode 60 into contact with the endocardium, in a direction parallel to the axis of the electrode assembly 36. A fixation sleeve 42, slidably mounted around lead body 22, serves to stabilize the pacing lead 20 at the site of venous insertion.

The electrode assembly 36 of FIG. 1 is shown in greater cross-sectional detail in FIG. 2. As illustrated, the electrode assembly 36 includes a conductive electrode 50 as well as the tine sheath 38 and the tines 40 thereof. The conductive electrode 50 is preferably a unitary construction including, at its proximal end, a cylindrical portion 52 defining an axial bore 54. A coil-wound conductor 56 of the lead body 22 of FIG. 1 is inserted into the axial bore 54 and affixed in electrical contact thereto, for example by crimping. Proceeding toward the distal end of the conductive electrode 50, the conductive electrode 50 includes a neck area 58 having a reduced diameter from the cylinder 52 which provides a recessed area into which an interior extending ridge of the tine sheath 38 is inserted to provide positive engagement of the tine sheath 38 with the conductive electrode 50. Finally, the conductive electrode 50 terminates at an electrode distal tip 60.

The electrode illustrated in FIG. 2 has a distal tip 60 with a generally mushroom shape, such that the electrode distal tip 60 has a semi-hemispherical surface which is intended to provide electrical contact with the endocardial tissue. It should be appreciated that the electrode distal tip 60 may define a number of different profiles, from semi-hemispherical to essentially planar with rounded edges. Examples of various preferred profiles are disclosed in detail in the assignee's copending application Ser. No. 07/892,463, filed Jun. 20, 1992, entitled "HIGH EFFICIENCY TISSUE STIMULATING AND SIGNAL SENSING ELECTRODE," herein incorporated by reference.

FIG. 3 shows an enlarged partial cross-sectional view of a portion of the electrode distal tip 60 enclosed in circle 3 of FIG. 2. As illustrated in FIG. 3, the electrode distal tip 60 includes the base metallic material 70, and a coating material 72. Preferably, the base metallic material 70 is a platinum-iridium alloy or similarly biocompatible, low polarization, conductive material. In the preferred embodiment, the platinum-iridium alloy has a composition of about 90% platinum and 10% iridium by weight.

The coating material 72 is selected for providing an electrically conductive, lubricating intermediate between the metallic material 70 and the endocardial tissue to reduce the tissue irritation and the inflammatory response. The coating material 72 can also be anti-inflammatory or hypo-inflammatory (i.e., a reduction in the inflammatory response). Thus, the coating material provides a means for delivering drugs or therapeutic agents, compounded into a matrix material of the coating material 72, by co-dissolution or diffusion. Accordingly, the coating material 72 is preferably a viscous or gelatinous matrix material compounded with an anti-inflammatory agent or drug. By comparison to a solid compound, the viscous or gelatinous matrix material is formulated so that it does not form a rigid structure or have a fixed crystalline lattice.

The coating material 72 is applied to the electrode distal tip 60 to thoroughly coat the distal tip 60 to a coating thickness in the range of between about 0.005 mm to 0.5 mm. Because of its viscous or gelatinous physical property, the coating material 72 may be readily applied by a number of known methods such as, for example, spraying or dipping. It should be noted that the coating material 72 is in the viscous or gelatinous state prior to implantation, and must be rehydrated if hardening has occurred during storage.

There are several considerations which must be addressed when choosing the constituents of the coating material 72. The three most important criteria are: (1) the coating material 72 must not affect the ability of the electrode to deliver a stimulus to the epicardium or myocardium, or to sense cardiac electrical activity; (2) the coating material 72 must allow for the delivery of some therapeutic agent by co-dissolution or diffusion, or alternatively the coating material 72 must possess hypo-inflammatory properties of its own; and (3) the coating material 72 should not dissolve upon implant and should remain intact through the acute inflammatory phase post-implant. Thus, the coating material 72, whether oligomeric, polymeric or monomeric, must not interfere with the ability of the conductive electrode 50 to deliver a stimulus or sense a cardiac signal while acting as an anti-inflammatory agent.

Accordingly, the coating material 72 has a viscous or gelatinous physical characteristic and exhibits the properties of biocompatibility and hydrophilicity. Materials which are hydrophilic will absorb water and become wet (like a sponge) this is due to constructive interactions of the matrix with electrolytes or physiological fluids at a molecular level. Absorption of physiologic fluids provides a low resistance conductive path, allowing current to be delivered through the coating material 72 to the abutting tissue of the epicardium or myocardium.

Preferred matrix materials which can be used as delivery systems or hypo-inflammatory coatings include soluble starches such as amylodextrin and amylogen, and proteins such as albumin, collagen, and gelatin. These proteins may be crosslinked with a crosslinking agent such as 1-ethyl-3-(3-dimethylaminopropyl)-carbodiimide, hydrochloride. These proteins are preferred because of the ability of the body to resorb them without adverse effect.

The preferred matrix materials exhibit a high degree of hydrophilicity. These materials can absorb in excess of fifty weight percent absorption of physiological fluid. The high degree of water absorption by the coating renders the biomaterial interfaces more compatible and thus should exhibit a hypo-inflammatory (i.e., a reduced inflammatory) characteristic post-injury. The acute and chronic threshold levels are thus lowered as a result of the increase in biocompatibility. Hydrophilic matrix materials are also preferred because they can be utilized for the transfer of therapeutic agents, preferably in their soluble salt forms, from within the hydrophilic matrix to the underlying tissue or physiologic environment.

Hydrophilic polymers can also be used as the matrix material. Preferred hydrophilic polymers are selected from the group including polyethylene oxide or glycol, polypropylene oxide or glycol, polysorbates, polyvinylalcohol, copolymers of ethylene oxide/propylene oxide, and cation exchange materials such as sulfonated polytetrafluoroethylene (as sold under the trade name NAFION, manufactured by DuPont). These hydrophilic polymers are easily absorbed by the body with no adverse effects and, advantageously, can deliver therapeutic agents by co-dissolution, diffusion, or resorption. Hydrophilic polymers which have been modified to incorporate a photo-activated or thermally-activated crosslinking moiety, such as polyethylene glycol (PEG), polyvinyl pyrrolidones (PVP), polyacrylmaide, and polyvinylalcohol (PVA) can also be utilized as coating materials. The advantage of these systems over non-crosslinked hydrophilic polymers is that the crosslinked materials will remain at the implant site for longer time periods due to diminished solubility. For example, polyethylene glycol (PEG), which has been modified to include photo-activated (photo-PEG) moieties, has been shown to be less soluble over longer periods of time. For a complete description of the modified PEG, photo-PEG, see copending U.S. patent application Ser. No. 07/960,669, filed concurrently herewith, which application is assigned to the same assignee and is hereby incorporated by reference.

The coating material 72 is preferably a mixture of one of the above matrix materials blended with an anti-inflammatory agent selected from the group including fluoro-trihydroxy-methyl pregna diene/dione or fluoro-methylprednisolone, sodium phosphate, the sodium salt of methoxy-methyl-naphthalene-acetic-acid, sodium, or the sodium salt of isobutylphenyl-propionic acid. Other anti-inflammatory or therapeutic agents compatible with the particular matrix material may also be utilized to form the coating material 72. The anti-inflammatory agents can constitute between about 0.5% to 50% by weight of the coating material 72, preferably however, the anti-inflammatory agents constitute in the range of between 5% and 50% by weight of the coating material 72 so as to not compromise the mechanical properties of the coating.

It is important to note that with many therapeutic agents, the solubility, especially in physiological fluid, can be manipulated by controlling cationic character. As an example, methoxy-methyl-naphthalene -acetic-acid, an anti-inflammatory agent containing a carboxylic acid moiety is quite insoluble in the acid form. However, upon an increase in the pH level, the acids are converted to the conjugate base or salt form. In the case of an anti-inflammatory agent such as the sodium salt of methoxy-methyl-naphthalene-acetic-acid, the converted agent becomes freely soluble. These two forms of the anti-inflammatory exhibit a similar anti-inflammatory response in humans; however, when both forms are blended together into a polymer matrix, which swells upon exposure to physiological fluid, these two forms demonstrate different rates of dissolution or diffusion. Thus, release rates of the anti-inflammatory agent from a variety of matrices can be manipulated by varying the therapeutic agent pH, matrix morphology, and the matrix material of choice.

In a preferred embodiment, the coating material 72 includes at least one anti-inflammatory agent carried in the matrix material, and the agent is itself a mixture of at least two different chemical forms of the agent having different rates of dissolution or diffusion. One example of a method of accomplishing this preferred embodiment is to use a blend of fifty percent methoxy -methyl-naphthalene-acetic-acid and fifty percent sodium salt of methoxy-methyl-naphthalene-acetic-acid. As can readily be appreciated, the relative percentages of these forms of the anti-inflammatory agent can be varied to cause the agent to be consumed at a faster or slower rate, as desired.

It should be evident from the foregoing description that the present invention provides many advantages over pacing leads of the prior art. Although preferred embodiments are specifically illustrated herein, it will be appreciated to those skilled in the art that many modifications and variations of the present invention are possible. Accordingly, the scope of the present invention is limited only by the proper scope of the appended claims.

What is claimed is:

1. An implantable stimulation lead adapted for electrical contact with heart tissue, said stimulation lead for use with a cardiac pulse generator, comprising:

an electrical conductor having a proximal end and a distal end;

an insulation sheath covering said conductor;

an electrode coupled to said distal end of said conductor for making electrical contact with heart tissue; and coating means coating said electrode for reducing inflammation of the heart tissue upon implant of the stimulation lead, said coating means including a viscous material coating, wherein said viscous material coating is a composition including a therapeutic agent and a biocompatible, matrix material comprising crosslinked proteins, wherein said proteins are selected from the group consisting of albumin, collagen and gelatin.

2. The implantable stimulation lead of claim 1, wherein said crosslinked proteins comprise proteins crosslinked with 1-ethyl-3-(3-dimethylaminopropyl)-carbodiimide hydrochloride.

3. An implantable stimulation lead adapted for electrical contact with heart tissue, said stimulation lead for use with a cardiac pulse generator, comprising:
an electrical conductor having a proximal end and a distal end;
an insulation sheath covering said conductor;
an electrode coupled to said distal end of said conductor for making electrical contact with heart tissue; and
coating means coating said electrode for reducing inflammation of the heart tissue upon implant of the stimulation lead, said coating means including a viscous material coating, wherein said viscous material coating is a composition including a therapeutic agent and a biocompatible, matrix material comprising a soluble starch selected from the group consisting of amylodextrin and amylogen.

4. An implantable stimulation lead adapted for electrical contact with heart tissue, said stimulation lead for use with a cardiac pulse generator, comprising:
an electrical conductor having a proximal end and a distal end;
an insulation sheath covering said conductor;
an electrode coupled to said distal end of said conductor for making electrical contact with heart tissue; and
coating means coating said electrode for reducing inflammation of the heart tissue upon implant of the stimulation lead, said coating means including a viscous material coating, wherein said viscous material coating is a biocompatible, matrix material comprising hydrophilic polymer derivatives selected from the group consisting of polyethylene glycols, polyvinylpyrrolidones, polyacrylamide, and polyvinylalcohol, wherein said hydrophilic polymer derivatives are modified to incorporate a photo-activated crosslinking moiety.

5. An implantable stimulation lead adapted for electrical contact with heart tissue, said stimulation lead for use with a cardiac pulse generator, comprising:
an electrical conductor having a proximal end and a distal end;
an insulation sheath covering said conductor;
an electrode coupled to said distal end of said conductor for making electrical contact with heart tissue; and
coating means coating said electrode for reducing inflammation of the heart tissue upon implant of the stimulation lead, said coating means including a viscous material coating, wherein said viscous material coating is a biocompatible, matrix material comprising hydrophilic polymer derivatives selected from the group consisting of polyethylene glycols, polyvinylpyrrolidones, polyacrylamide, and polyvinylalcohol, wherein said hydrophilic polymer derivatives are modified to incorporate a thermally-activated crosslinking moiety.

* * * * *